United States Patent
Popp et al.

(10) Patent No.: US 8,007,485 B2
(45) Date of Patent: Aug. 30, 2011

(54) MECHANICAL FASTENING SYSTEM FOR AN ABSORBENT ARTICLE

(75) Inventors: Robert L. Popp, Hortonville, WI (US); Debra Durrance, Appleton, WI (US); Paul VanGompel, Hortonville, WI (US); Michael T. Morman, Alpharetta, GA (US); Paul M. Linker, Appleton, WI (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 1733 days.

(21) Appl. No.: 10/036,573

(22) Filed: Dec. 31, 2001

(65) Prior Publication Data

US 2003/0125703 A1    Jul. 3, 2003

(51) Int. Cl.
*A61F 13/15* (2006.01)
*A61F 13/20* (2006.01)
*B32B 3/06* (2006.01)

(52) U.S. Cl. .................. 604/391; 604/386; 604/385.01; 428/99

(58) Field of Classification Search .................. 604/391, 604/386, 385.01; 428/198, 152, 99; 442/364, 442/328
See application file for complete search history.

(56) References Cited

U.S. PATENT DOCUMENTS

| | | | |
|---|---|---|---|
| 2,957,512 A | 10/1960 | Wade et al. | |
| 3,319,307 A | 5/1967 | Marforio | |
| 3,577,607 A | 5/1971 | Ikoma et al. | |
| 3,943,981 A | 3/1976 | DeBrabander | |
| 4,035,559 A | 7/1977 | Fujii et al. | |
| 4,205,679 A | 6/1980 | Repke et al. | |
| 4,606,964 A | 8/1986 | Wideman | |
| 4,610,680 A | 9/1986 | LaFleur | |
| 4,615,695 A | 10/1986 | Cooper | |
| 4,657,802 A | 4/1987 | Morman | |
| 4,699,622 A | 10/1987 | Toussant et al. | |
| 4,705,710 A | 11/1987 | Matsuda | |
| 4,714,096 A | 12/1987 | Guay | |
| 4,761,318 A | 8/1988 | Ott et al. | |

(Continued)

FOREIGN PATENT DOCUMENTS

EP    0 289 198 A1    11/1988

(Continued)

OTHER PUBLICATIONS

International Search Report for PCT/US 02/37893 dated Jun. 23, 2003, 7 pgs.

(Continued)

*Primary Examiner* — Leslie R Deak
*Assistant Examiner* — Susan Su
(74) *Attorney, Agent, or Firm* — Armstrong Teasdale LLP

(57) ABSTRACT

In a mechanical fastening system for an article, a first fastening component of the fastening system is constructed of an oriented nonwoven loop material. The nonwoven loop material is constructed at least part of an nonwoven web of fibers that is extensible from a relaxed configuration to an extended configuration wherein in the extended configuration a greater number of fibers of the nonwoven web are oriented in the direction in which the web is extended than in the relaxed configuration of the web. In one embodiment, the web is in its extended configuration and secured to a substrate A second fastening component of the mechanical fastening system comprises a hook material wherein the oriented nonwoven loop material of the first fastening component is adapted for releasable connection with the hook material of the second fastening component.

14 Claims, 8 Drawing Sheets

U.S. PATENT DOCUMENTS

| | | | |
|---|---|---|---|
| 4,826,499 A | | 5/1989 | Ahr |
| 4,834,741 A | * | 5/1989 | Sabee ................. 604/385.29 |
| 4,834,742 A | | 5/1989 | Wilson et al. |
| 4,847,134 A | | 7/1989 | Fahrenkrug et al. |
| 4,850,990 A | | 7/1989 | Huntoon et al. |
| 4,894,060 A | | 1/1990 | Nestegard |
| 4,940,464 A | | 7/1990 | Van Gompel et al. |
| 4,963,140 A | | 10/1990 | Robertson et al. |
| 4,965,122 A | * | 10/1990 | Morman ................. 442/328 |
| 4,981,747 A | * | 1/1991 | Morman ................. 428/198 |
| 5,019,073 A | | 5/1991 | Roessler et al. |
| 5,032,120 A | | 7/1991 | Freeland et al. |
| 5,032,122 A | | 7/1991 | Noel et al. |
| 5,087,253 A | | 2/1992 | Cooper |
| 5,114,781 A | * | 5/1992 | Morman ................. 428/198 |
| 5,116,662 A | * | 5/1992 | Morman ................. 428/198 |
| 5,143,679 A | * | 9/1992 | Weber et al. ............. 264/288.8 |
| 5,176,671 A | | 1/1993 | Roessler et al. |
| 5,226,992 A | | 7/1993 | Morman |
| 5,236,430 A | * | 8/1993 | Bridges ................. 604/396 |
| 5,256,231 A | | 10/1993 | Gorman et al. |
| 5,318,555 A | | 6/1994 | Siebers et al. |
| 5,326,612 A | | 7/1994 | Goulait |
| 5,336,545 A | * | 8/1994 | Morman ................. 428/152 |
| 5,370,634 A | | 12/1994 | Ando et al. |
| 5,374,262 A | | 12/1994 | Keuhn, Jr. et al. |
| 5,380,313 A | | 1/1995 | Goulait et al. |
| 5,383,872 A | | 1/1995 | Roessler et al. |
| 5,386,595 A | | 2/1995 | Kuen et al. |
| 5,407,439 A | | 4/1995 | Goulait |
| 5,453,318 A | | 9/1995 | Giacobbe |
| 5,547,531 A | | 8/1996 | Allen et al. |
| 5,595,567 A | | 1/1997 | King et al. |
| 5,614,281 A | | 3/1997 | Jackson et al. |
| 5,615,460 A | | 4/1997 | Weirich et al. |
| 5,616,394 A | | 4/1997 | Gorman et al. |
| 5,622,578 A | | 4/1997 | Thomas |
| 5,624,427 A | * | 4/1997 | Bergman et al. ............. 604/391 |
| 5,628,741 A | | 5/1997 | Buell et al. |
| 5,647,864 A | | 7/1997 | Allen et al. |
| 5,664,302 A | | 9/1997 | Thomas |
| 5,669,900 A | | 9/1997 | Bullwinkel et al. |
| 5,669,901 A | | 9/1997 | LaFortune et al. |
| 5,681,302 A | | 10/1997 | Melbye et al. |
| 5,693,401 A | | 12/1997 | Sommers et al. |
| 5,707,707 A | | 1/1998 | Burnes et al. |
| 5,735,840 A | | 4/1998 | Kline et al. |
| 5,763,041 A | | 6/1998 | Leak et al. |
| 5,766,389 A | | 6/1998 | Brandon et al. |
| 5,785,699 A | | 7/1998 | Schmitz |
| 5,795,350 A | | 8/1998 | Schmitz |
| 5,830,206 A | | 11/1998 | Larsson |
| 5,830,298 A | | 11/1998 | Jackson |
| 5,853,881 A | * | 12/1998 | Estey et al. ................. 428/373 |
| 5,855,574 A | | 1/1999 | Kling et al. |
| 5,858,515 A | | 1/1999 | Stokes et al. |
| 5,867,925 A | | 2/1999 | Fattori |
| 5,883,028 A | * | 3/1999 | Morman et al. ............. 442/394 |
| 5,888,607 A | | 3/1999 | Seth et al. |
| 5,891,547 A | | 4/1999 | Lawless |
| 5,897,547 A | | 4/1999 | Schmitz |
| 5,901,419 A | | 5/1999 | Widlund et al. |
| 5,910,136 A | * | 6/1999 | Hetzler et al. ............. 604/367 |
| 5,914,084 A | * | 6/1999 | Benson et al. ............. 264/284 |
| 5,938,648 A | | 8/1999 | LaVon et al. |
| 5,953,797 A | | 9/1999 | Provost et al. |
| 6,018,852 A | | 2/2000 | Coslovi et al. |
| 6,027,485 A | | 2/2000 | Matsushita et al. |
| 6,036,805 A | | 3/2000 | McNichols |
| 6,086,571 A | | 7/2000 | Guevara et al. |
| 6,102,901 A | | 8/2000 | Lord et al. |
| 6,113,717 A | | 9/2000 | Vogt et al. |
| 6,136,405 A | | 10/2000 | Young et al. |
| 6,142,986 A | | 11/2000 | Lord et al. |
| 6,146,738 A | | 11/2000 | Tsuji et al. |
| 6,150,002 A | | 11/2000 | Varona |
| 6,192,556 B1 | | 2/2001 | Kikko et al. |
| 6,197,404 B1 | | 3/2001 | Varona |
| 6,210,389 B1 | | 4/2001 | Long et al. |
| 6,287,287 B1 | | 9/2001 | Elsberg |
| 6,328,725 B2 | | 12/2001 | Fernfors |
| 6,329,016 B1 | | 12/2001 | Shepard et al. |
| 6,332,250 B1 | | 12/2001 | Igaue et al. |
| 6,417,121 B1 | * | 7/2002 | Newkirk et al. ............. 442/364 |
| 6,417,122 B1 | * | 7/2002 | Newkirk et al. ............. 442/364 |
| 6,420,285 B1 | * | 7/2002 | Newkirk et al. ............. 442/364 |
| 6,461,344 B1 | | 10/2002 | Widlund et al. |
| 6,475,600 B1 | | 11/2002 | Morman et al. |
| 6,647,549 B2 | | 11/2003 | McDevitt et al. |
| 2002/0173767 A1 | | 11/2002 | Popp et al. |
| 2003/0045856 A1 | | 3/2003 | Couture et al. |

FOREIGN PATENT DOCUMENTS

| | | |
|---|---|---|
| EP | 0 463 276 A1 | 1/1992 |
| EP | 0 638 304 | 2/1995 |
| EP | 0 782 424 | 7/1997 |
| EP | 0 800 379 | 10/1997 |
| EP | 0812584 A2 | 12/1997 |
| FR | 1.371.254 | 9/1964 |
| GB | 2 387 180 A | 10/2003 |
| WO | WO 92/01401 A1 | 2/1992 |
| WO | WO 96/03101 A1 | 2/1996 |
| WO | WO 97/19808 A1 | 6/1997 |
| WO | WO 97/25893 A1 | 7/1997 |
| WO | WO 98/29503 A1 | 7/1998 |
| WO | WO 98/29504 A1 | 7/1998 |
| WO | WO 99/14045 A1 | 3/1999 |
| WO | WO 99/65441 | 12/1999 |
| WO | WO 00/35395 | 6/2000 |
| WO | WO 00/35398 | 6/2000 |
| WO | WO 00/37009 | 6/2000 |
| WO | WO 01/87206 A1 | 11/2001 |
| WO | WO 01/87208 A1 | 11/2001 |
| WO | WO 01/87209 A1 | 11/2001 |
| WO | WO 01/87753 A2 | 11/2001 |

OTHER PUBLICATIONS

International Search Report for PCT/US 02/37896 dated Jun. 11, 2003.

International Search Report for PCT/US 02/40780 dated Apr. 22, 2003.

* cited by examiner

MECHANICAL FASTENING SYSTEM FOR AN ABSORBENT ARTICLE

BACKGROUND OF THE INVENTION

The present invention pertains to absorbent articles, such as training pants, diapers, incontinence garments and the like, and more particularly, to a mechanical fastening system for such absorbent articles.

Such absorbent articles generally comprise a liquid-impermeable barrier sheet, a liquid permeable body side liner and an absorbent medium between them. They generally include some type of attaching system for fitting the article to the wearer. In many such applications, the fastening system is preferably refastenable so that the article can be temporarily removed and then refastened to the wearer.

Common forms of mechanical fastening systems are the so called hook-and-loop systems which come in various forms and have both advantages and disadvantages in their application to such absorbent articles. For example, particularly with diapers, the fasteners are secured to both sides of the garment on the front and back thereof, generally in such a manner that the back portion of the fasteners on each side are pulled over the front portion to secure the garment to the wearer. In typical such products, the loop materials are generally non-extensible and are attached to the surface of the garment. The hook material is generally attached to an extensible substrate so that it can be positioned on the loop material for adjustment to the size and shape of the wearer of the garment.

A disadvantage of this type of hook-and-loop system is the tendency of the hooks to separate from the loop material when the wearer is active, such as when stooping or bending as is common with a child. This disengagement failure results in the garment coming loose from the wearer (with possible leakage resulting) thus requiring it to be refastened, if possible. This produces an undesirable inconvenience and disadvantage of such a mechanical fastening system for such applications.

Another disadvantage of this type of hook-and-loop system is the generally high cost of the materials, which tends to constrain the size and construction of the fastening elements used in disposable applications and may constitute a compromise in performance. Woven or knitted loop materials are well-known and commonly available, but are very expensive. Nonwoven loop materials are much less costly, but are not available widely or with a wide range of properties or applicability.

SUMMARY OF THE INVENTION

The present invention overcomes the above-described difficulties and disadvantages associated with such prior art mechanical fastening systems by providing a hook-and-loop fastening system in which the loop material is a material made of an oriented nonwoven. The oriented non-woven can be stabilized if necessary by laminating to another layer or by thermally setting the material. The orientation of the non-woven layer makes the individual fibers of a randomly formed nonwoven align in a more parallel fashion. This loop material can be used for making many products such as a disposable training pant, a disposable diaper, or the like. This loop material can be elastic or inelastic, depending on how it is treated, combined with other materials, or applied to a product.

Thus, one aspect of the present invention relates to mechanical fastening systems for an article. In one embodiment, the mechanical fastening system comprises: a first fastening component comprising an oriented nonwoven loop material disposed on an article, the oriented nonwoven loop material comprising a nonwoven web and produced by application of a force causing constituent fibers of the nonwoven web to become oriented in a direction of the applied force without substantial necking or gathering of the nonwoven web in a direction perpendicular to the applied force; and a second fastening component comprising a hook material disposed on the article and adapted to engage the first fastening component.

In another embodiment, the mechanical fastening system comprises: a first fastening component comprising an oriented nonwoven loop material disposed on an article, the oriented nonwoven loop material comprising a nonwoven web and produced by application of a force causing constituent fibers of the nonwoven web to become oriented in a direction of the applied force, the first fastening component having been stabilized by laminating the oriented nonwoven loop material to an inelastic material; and a second fastening component comprising a hook material disposed on the article and adapted to engage the first fastening component.

The oriented nonwoven loop materials find particular usefulness on disposable absorbent articles, and thus another aspect of the invention relates to disposable absorbent articles. In one embodiment, a disposable absorbent article for personal wear comprises: a body having first and second end regions and comprising a liquid permeable inner layer for contact with the wearer's skin, an outer layer in opposed relation with the inner layer, and an absorbent layer disposed between the inner layer and the outer layer; and a mechanical fastening system comprising first and second fastening components disposed in the respective first and second end regions and adapted to refastenably secure the body in a pant configuration, the first fastening component formed of an oriented nonwoven loop material comprising a nonwoven web, the oriented nonwoven loop material produced by application of a force causing constituent fibers of the nonwoven web to become oriented in a direction of the applied force, the first fastening component being extensible and bonded in overlaying relationship onto a layer of the body to retain extension and retraction characteristics of oriented nonwoven loop material, and the second fastening component comprising a hook material.

This invention uses an elastic or inelastic loop material constructed from an oriented nonwoven secured directly to an article or to an elastic or inelastic material to provide fiber loops accessible to the hook material and with sufficient integrity to withstand engagement. Control of the degree of orientation and/or necking and/or addition of patterned bonds to the oriented material can further be used to modify the material characteristics, and thus, its engagement characteristics. For example, by controlling the hook size and the degree of necking independently, it is possible to produce fastening systems that provide the above mentioned product.

Hence, the present invention also concerns method of making mechanical fastening systems for articles. In one embodiment, a method of making a mechanical fastening system for an article comprises: forming an oriented nonwoven loop material from a nonwoven web of substantially continuous fibers by drawing the nonwoven web using an applied force to align constituent fibers of the nonwoven web without substantial necking or gathering of the nonwoven web in a direction perpendicular to the applied force; and disposing the drawn nonwoven web on a disposable absorbent article.

In another embodiment, a method of making a mechanical fastening system for an article comprises: forming an oriented nonwoven loop material from a nonwoven web of substantially continuous fibers by drawing the nonwoven web using an applied force to align the constituent fibers of the nonwoven web, and bonding the drawn nonwoven web in overlaying relationship onto a layer of a disposable absorbent article to retain extension and retraction characteristics of oriented nonwoven loop material.

In a further embodiment, a method of making a mechanical fastening system for an article comprises: forming an oriented nonwoven loop material from a nonwoven web of substantially continuous fibers by drawing the nonwoven web using an applied force to align the constituent fibers of the nonwoven web, laminating the oriented nonwoven loop material to an inelastic material, and disposing the drawn nonwoven laminate on a disposable absorbent article.

BRIEF DESCRIPTION OF THE DRAWINGS

The above-mentioned and other features of the present invention, and the manner of obtaining them, will become more apparent and the invention itself will be better understood by reference to the following description of the embodiments of the invention taken in conjunction with the accompanying drawings, wherein.

Corresponding reference characters indicate corresponding parts throughout the drawings.

Definitions

Figure 1:
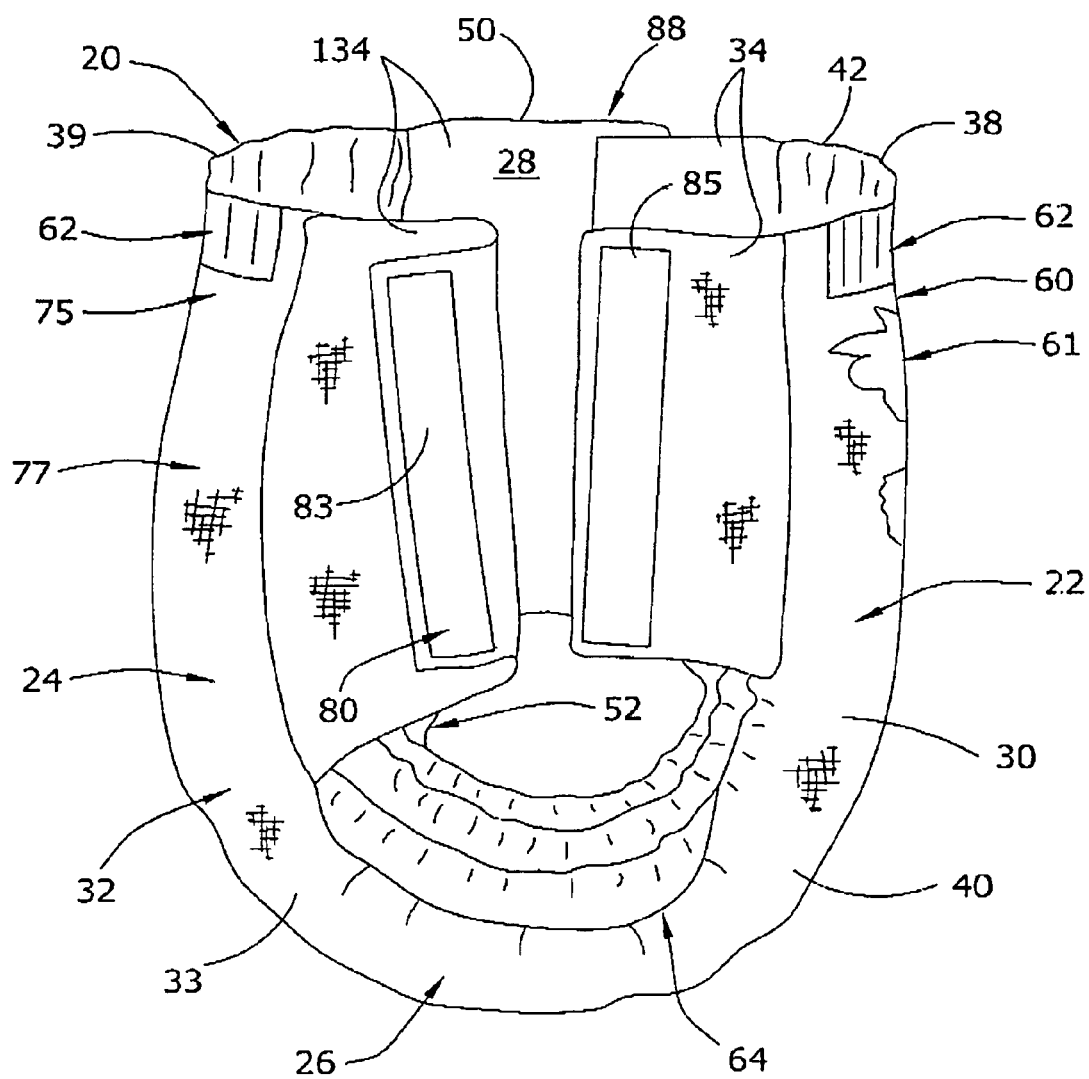
FIG. 1 illustrates a side view of a training pant suitable for use with the process and apparatus according to the present invention, where the fastening system is shown engaged on one side of the training pant and disengaged on the other side of the training pant.

Within the context of this specification, each term or phrase below will include the following meaning or meanings.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Comprising" is inclusive or open-ended and does not exclude additional, unrecited elements or method steps.

"Connected" refers to the joining, adhering, bonding, attaching, or the like, of two elements. Two elements will be considered to be connected together when they are connected directly to one another or indirectly to one another, such as when each is directly connected to intermediate elements.

"Disposable" refers to articles which are designed to be discarded after a limited use rather than being laundered or otherwise restored for reuse.

"Disposed," "disposed on," and variations thereof are intended to mean that one element can be integral with another element, or that one element can be a separate structure bonded to or placed with or placed near another element.

"Elastic," "elasticized" and "elasticity" mean that property of a material or composite by virtue of which it tends to recover its original size and shape after removal of a force causing a deformation.

"Elastomeric" refers to a material or composite which can be elongated by at least 25 percent of its relaxed length and which will recover, upon release of the applied force, at least 10 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Extensible" refers to a material or composite that is stretchable or capable of being elongated in at least one direction, but which may not have sufficient recovery to be considered elastic.

"Fabrics" is used to refer to all of the woven, knitted and nonwoven fibrous webs.

"Flexible" refers to materials which are compliant and which will readily conform to the general shape and contours of the wearer's body.

"Force" includes a physical influence exerted by one body on another which produces acceleration of bodies that are free to move and deformation of bodies that are not free to move.

"Graphic" refers to any design, pattern, or the like that is visible on an absorbent article.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90 are designated "wettable" or hydrophilic, while fibers having contact angles greater than 90 are designated "nonwettable" or hydrophobic.

"Integral" is used to refer to various portions of a single unitary element rather than separate structures bonded to or placed with or placed near one another.

"Inward" and "outward" refer to positions relative to the center of an absorbent article, and particularly transversely and/or longitudinally closer to or away from the longitudinal and transverse center of the absorbent article.

"Layer" when used in the singular can have the dual meaning of a single element or a plurality of elements.

"Liquid impermeable", when used in describing a layer or multi-layer laminate, means that a liquid, such as urine, will not pass through the layer or laminate, under ordinary use conditions, in a direction generally perpendicular to the plane of the layer or laminate at the point of liquid contact. Liquid, or urine, may spread or be transported parallel to the plane of the liquid impermeable layer or laminate, but this is not considered to be within the meaning of "liquid impermeable" when used herein.

Figure 2:
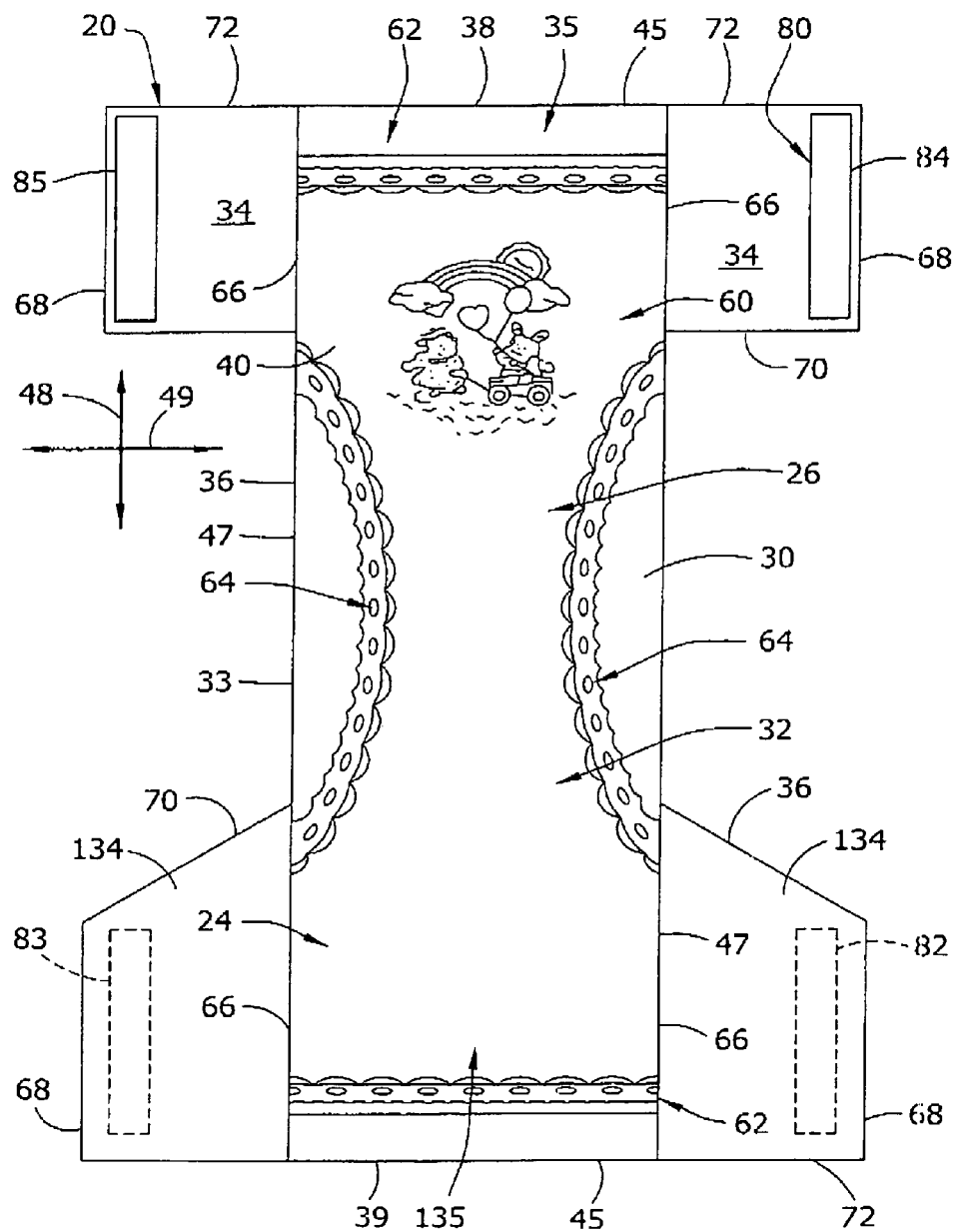
FIG. 2 illustrates a plan view of the training pant shown in FIG. 1 in an unfastened, stretched and laid flat condition, and showing the surface of the training pant that faces away from the wearer.
Figure 3:
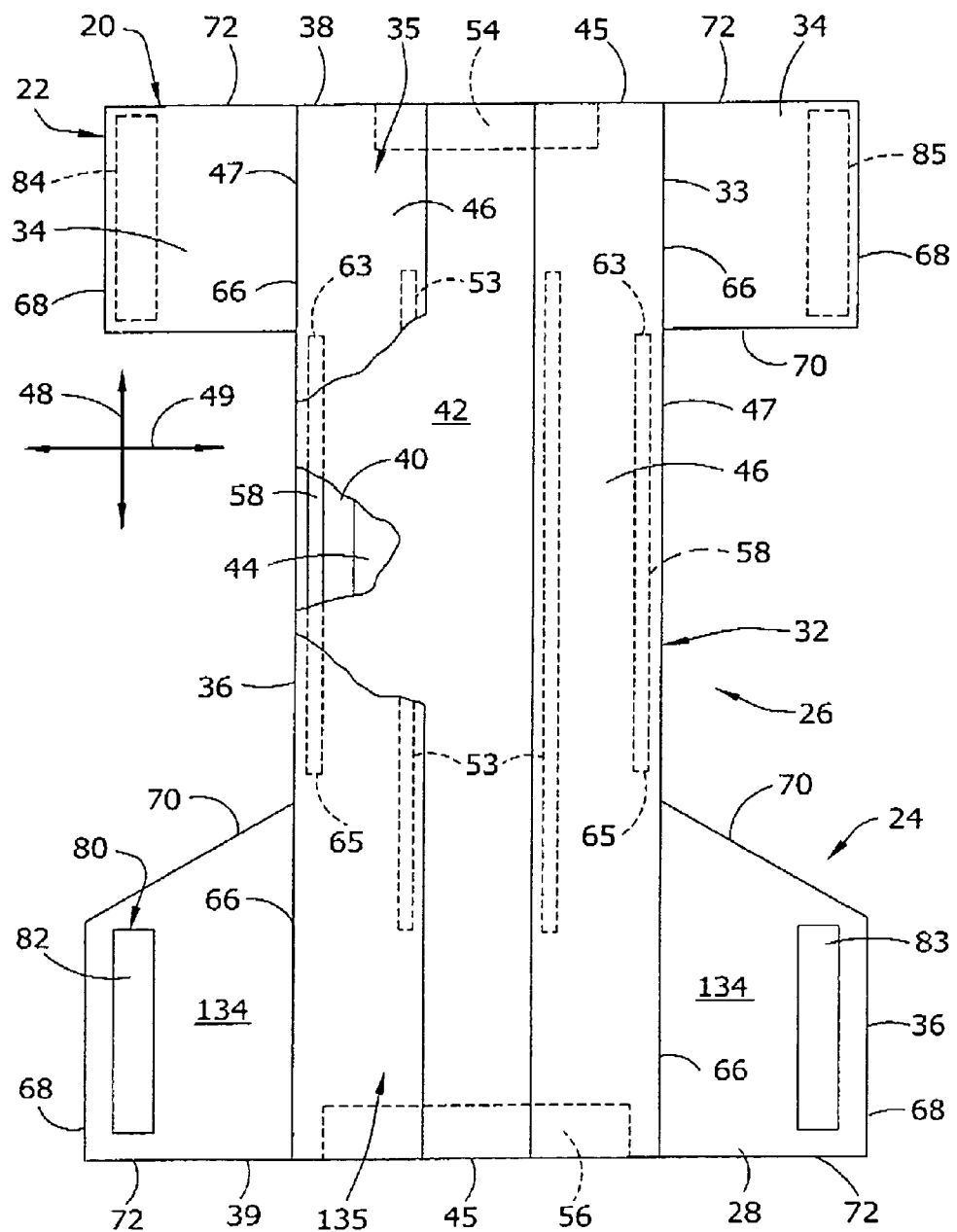
FIG. 3 illustrates a plan view similar to FIG. 2, but showing the surface of the training pant that faces the wearer when the training pant is worn, and with portions cut away to show the underlying features.

"Longitudinal" and "transverse" have their customary meaning, as indicated by the longitudinal and transverse axes depicted in FIGS. 2 and 3. The longitudinal axis lies in the plane of the article and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction.

"Member" when used in the singular can have the dual meaning of a single element or a plurality of elements.

"Nonwoven" and "nonwoven web" refer to materials and webs of material which are formed without the aid of a textile weaving or knitting process.

"Operatively joined," with reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

"Outer cover graphic" refers to a graphic that is directly visible upon inspection of the exterior surface of a garment, and for a refastenable garment is in reference to inspection of the exterior surface of the garment when the fastening system is engaged as it would be during use.

"Permanently bonded" refers to the joining, adhering, connecting, attaching, or the like, of two elements of an absorbent garment such that the elements tend to be and remain bonded during normal use conditions of the absorbent garment.

"Refastenable" refers to the property of two elements being capable of attachment, separation, and subsequent reattachment.

"Releasably attached," "releasably engaged" and variations thereof refer to two elements being connected or connectable such that the elements tend to remain connected absent a separation force applied to one or both of the elements, and the elements being capable of separation without substantial permanent deformation or rupture. The required separation force is typically beyond that encountered while wearing the absorbent garment.

"Necked material" refers to a material that has been extended under mechanical force in one direction substantially beyond its tensile yield point in that direction in a manner that narrows, or "necks" the material in the direction perpendicular to the direction of the applied force so that the material does not tend to recover to its original width dimension.

"Oriented nonwoven loop material" refers to a web comprising fibers or filaments that is formed other than by weaving or knitting. The fibers in the web have a generally random orientation except that more of the fibers are generally parallel to a direction corresponding to a direction of force previously applied to the web. More fibers in the web are oriented in the direction of force after application of force than before application of force. Thus, the force alters the orientation of at least some of the fibers in the web causing the altered fibers to align generally in the direction of force.

"Oriented material" refers to a material in which mechanical drawing of the material has resulted in alignment of the fibers constituting the material in a direction generally parallel to the direction of the applied force.

"Reversibly necked material" refers to a necked material that has been treated while necked to impart memory to the material so that, when a force is applied to extend the material to its pre-necked dimensions, the necked and treated portions will generally recover to their necked dimensions upon termination of the force. One form of treatment is the application of heat. Generally speaking, extension of the reversibly necked material is substantially limited to extension to its pre-necked dimensions. Therefore, unless the material is elastic, extension too far beyond its pre-necked dimensions will result in material failure. A reversibly necked material may include more than one layer, for example, multiple layers of spunbonded web, multiple layers of meltblown web, or any other suitable combinations or mixtures thereof.

"Rupture" means the breaking or tearing apart of a material; in tensile testing, the term refers to the total separation of a material into two parts either all at once or in stages, or the development of a hole in some materials.

"Stretch bonded" refers to an elastic member being bonded to another member while the elastic member is extended at least about 25 percent of its relaxed length. Desirably, the term "stretch bonded" refers to the situation wherein the elastic member is extended at least about 100 percent, and more desirably at least about 300-600 percent, of its relaxed length when it is bonded to the other member.

"Stretch bonded laminate" refers to a composite material having at least two layers in which one layer is a gatherable layer and the other layer is an elastic layer. The layers are joined together when the elastic layer is in an extended condition so that upon relaxing the layers, the gatherable layer is gathered.

"Surface" includes any layer, film, woven, nonwoven, laminate, composite, or the like, whether pervious or impervious to air, gas, and/or liquids.

"Tension" includes a uniaxial force tending to cause the extension of a body or the balancing force within that body resisting the extension.

"Thermoplastic" describes a material that softens when exposed to heat and which substantially returns to a non-softened condition when cooled to room temperature.

These terms may be defined with additional language in the remaining portions of the specification.

DETAILED DESCRIPTION OF THE PREFERRED EMBODIMENTS

FIG. 1 representatively illustrates one embodiment of training pant 20 in a partially fastened condition. The training pant 20 comprises an absorbent body 32 and a fastening system 80. The absorbent body 32 defines a front waist region 22, a back waist region 24, a crotch region 26 interconnecting the front and back waist regions, an inner surface 28 which is configured to contact the wearer, and an outer surface 30 opposite the inner surface which is configured to contact the wearer's clothing. With additional reference to FIGS. 2 and 3, the absorbent body 32 also defines a pair of transversely opposed side edges 36 and a pair of longitudinally opposed waist edges, which are designated front waist edge 38 and back waist edge 39. The front waist region 22 is contiguous with the front waist edge 38, and the back waist region 24 is contiguous with the back waist edge 39.

The illustrated absorbent body 32 comprises a rectangular composite structure 33, a pair of transversely opposed front side panels 34, and a pair of transversely opposed back side panels 134. The composite structure 33 and side panels 34 and 134 may be integrally formed or comprise two or more separate elements, as shown in FIG. 1. The illustrated composite structure 33 comprises an outer cover 40, a body side liner 42 (FIG. 3) which is connected to the outer cover in a superposed relation, an absorbent assembly 44 (FIG. 3) which is located between the outer cover and the body side liner, and a pair of containment flaps 46 (FIG. 3). The illustrated composite structure 33 has opposite linear end edges 45 that form portions of the front and back waist edges 38 and 39, and opposite linear side edges 47 that form portions of the side edges 36 of the absorbent body 32 (FIGS. 2 and 3). For reference, arrows 48 and 49 depicting the orientation of the longitudinal axis and the transverse axis, respectively, of the training pant 20 are illustrated in FIGS. 2 and 3.

With the training pant 20 in the fastened position as partially illustrated in FIG. 1, the front and back waist regions 22 and 24 are joined together to define a three-dimensional pant configuration having a waist opening 50 and a pair of leg openings 52. The front waist region 22 comprises the portion of the training pant 20 which, when worn, is positioned on the front of the wearer while the back waist region 24 comprises the portion of the training pant which, when worn, is positioned on the back of the wearer. The crotch region 26 of the training pant 20 comprises the portion of the training pant which, when worn, is positioned between the legs of the wearer and covers the lower torso of the wearer. The front and back side panels 34 and 134 comprise the portions of the training pant 20 which, when worn, are positioned on the hips of the wearer.

The front waist region 22 of the absorbent body 32 includes the transversely opposed front side panels 34 and a front center panel 35 (FIGS. 2 and 3) positioned between and interconnecting the side panels. The back waist region 24 of the absorbent body 32 includes the transversely opposed back side panels 134 and a back center panel 135 (FIGS. 2 and 3) positioned between and interconnecting the side panels. The waist edges 38 and 39 of the absorbent body 32 are configured to encircle the waist of the wearer when worn and provide the waist opening 50 which defines a waist perimeter dimension. Portions of the transversely opposed side edges 36 in the crotch region 26 generally define the leg openings 52. The waist regions 22 and 24 jointly define a waistband 75 (FIGS. 1, 4 and 7) that peripherally surrounds the waist opening 50 of the pant 20. The waist regions 22 and 24 also jointly define a hip section 77 (FIGS. 1, 4 and 7) that encircles the pant 20 and is disposed between the waistband 75 and the leg openings 52.

The absorbent body 32 is configured to contain and/or absorb any body exudates discharged from the wearer. For example, the absorbent body 32 desirably although not necessarily comprises the pair of containment flaps 46 which are configured to provide a barrier to the transverse flow of body exudates. A flap elastic member 53 (FIG. 3) is operatively joined with each containment flap 46 in any suitable manner as is well known in the art. The elasticized containment flaps 46 define an unattached edge which assumes an upright configuration in at least the crotch region 26 of the training pant 20 to form a seal against the wearer's body. The containment flaps 46 can be located along the transversely opposed side edges of the absorbent body 32, and can extend longitudinally along the entire length of the absorbent body or may only extend partially along the length of the absorbent body. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the training pant 20 desirably although not necessarily includes a front waist elastic member 54, a rear waist elastic member 56, and leg elastic members 58, as are known to those skilled in the art (FIG. 3). The waist elastic members 54 and 56 can be operatively joined to the outer cover 40 and/or body side liner 42 along the opposite waist edges 38 and 39, and can extend over part or all of the waist edges, such that the waist elastic members are disposed in the waistband 75 in the fully assembled pant.

The leg elastic members 58 are desirably operatively joined to the outer cover 40 and/or body side liner 42 along the opposite side edges 36 and positioned in the crotch region 26 of the training pant 20. The leg elastic members 58 can be longitudinally aligned along each side edge 47 of the composite structure 33. Each leg elastic member 58 has a front terminal point 63 and a back terminal point 65, which points represent the longitudinal ends of the elastic gathering caused by the leg elastic members. The front terminal points 63 can be located adjacent the longitudinally innermost parts of the front side panels 34, and the back terminal points 65 can be located adjacent the longitudinally innermost parts of the back side panels 134.

The flap elastic members 53, the waist elastic members 54 and 56, and the leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the leg elastic members 58 comprise a plurality of dry-spun coalesced multifilament spandex elastomeric threads sold under the trade name LYCRA and available from E. I. DuPont de Nemours and Company, Wilmington, Del. U.S.A.

In particular embodiments, the waist elastic members 54 and 56 can be formed of retractive materials. For example, the waist elastic members 54 and 56 can be formed of an elastomeric material that is adapted to retract upon activation by a source of heat such as disclosed in U.S. Pat. No. 4,640,726.

The outer cover 40 desirably comprises a material that is substantially liquid impermeable, and can be elastic or inelastic. The outer cover 40 can be a single layer of liquid impermeable material, but desirably comprises a multi-layered laminate structure in which at least one of the layers is liquid impermeable. For instance, the outer cover 40 can include a liquid permeable outer layer and a liquid impermeable inner layer that are suitably joined together by laminate adhesive, ultrasonic bonds, thermal bonds, or the like. Suitable laminate adhesives, which can be applied continuously or intermittently as beads, a spray, parallel swirls, or the like, can be obtained from Findley Adhesives, Inc., of Wauwatosa, Wis. U.S.A., or from National Starch and Chemical Company, Bridgewater, N.J. U.S.A. The liquid permeable outer layer can be any suitable material and desirably one that provides a generally cloth-like texture. One example of such a material is a 20 gsm (grams per square meter) spunbond polypropylene nonwoven web. The outer layer may also be made of an oriented nonwoven material as provided by this invention, constituting an integral and functional loop material covering the entire outer surface of the cover 40. While it is not a necessity for outer layer to be liquid permeable, it is desired that it provides a relatively cloth-like texture to the wearer.

The inner layer of the outer cover 40 can be both liquid and vapor impermeable, or can be liquid impermeable and vapor permeable. The inner layer is desirably manufactured from a thin plastic film, although other flexible liquid impermeable materials may also be used. The inner layer, or the liquid impermeable outer cover 40 when a single layer, prevents waste material from wetting articles, such as bed sheets and clothing, as well as the wearer and caregiver. A suitable liquid impermeable film for use as a liquid impermeable inner layer, or a single layer liquid impermeable outer cover 40, is a 0.02 millimeter polyethylene film commercially available from Huntsman Packaging of Newport News, Va. U.S.A. If the outer cover 40 is a single layer of material, it can be embossed and/or matte finished providing a more cloth-like appearance. As earlier mentioned, the liquid impermeable material can permit vapors to escape from the interior of the disposable absorbent article, while still preventing liquids from passing through the outer cover 40. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn. U.S.A.

As shown in FIGS. 1 and 2, the training pant 20 and in particular the outer cover 40 desirably comprises one or more appearance-related components. Examples of appearance-related components include, but are not limited to, graphics; highlighting or emphasizing leg and waist openings in order to make product shaping more evident or visible to the user; highlighting or emphasizing areas of the product to simulate functional components such as elastic leg bands, elastic waistbands, simulated fly openings for boys, ruffles for girls; highlighting areas of the product to change the appearance of the size of the product; registering wetness indicators, temperature indicators, and the like in the product; registering a back label, or a front label, in the product; and registering written instructions at a desired location in the product.

The illustrated training pant 20, which is designed for use by young girls, includes a registered outer cover graphic 60. In this design, the registered graphic 60 includes a primary pictorial image 61, simulated waist ruffles 62, and simulated leg ruffles 64. The primary pictorial image 61 includes a rainbow, sun, clouds, animal characters, wagon and balloons. Any suitable design can be utilized for a training pant intended for use by young girls, so as to be aesthetically and/or functionally pleasing to them and the caregiver. The appearance-related components are desirably positioned on the training pant 20 at selected locations, which can be carried out using the methods disclosed in U.S. Pat. No. 5,766,389 issued Jun. 16, 1998 to Brandon et al., which is incorporated herein by reference. The primary pictorial image 61 is desirably positioned in the front waist region 22 along the longitudinal centerline of the training pant 20.

The liquid permeable body side liner 42 is illustrated as overlying the outer cover 40 and absorbent assembly 44, and may but need not have the same dimensions as the outer cover 40. The body side liner 42 is desirably compliant, soft feeling, and non-irritating to the child's skin. Further, the body side liner 42 can be less hydrophilic than the absorbent assembly 44, to present a relatively dry surface to the wearer and permit liquid to readily penetrate through its thickness. Alternatively, the body side liner 42 can be more hydrophilic or can have essentially the same affinity for moisture as the absorbent assembly 44 to present a relatively wet surface to the wearer to increase the sensation of being wet. This wet sensation can be useful as a training aid. The hydrophilic/hydrophobic properties can be varied across the length, width and depth of the body side liner 42 and absorbent assembly 44 to achieve the desired wetness sensation or leakage performance.

The body side liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the body side liner 42. For example, the body side liner can be composed of a meltblown or spunbonded web of polyolefin fibers. The body side liner can also be a bonded-carded web composed of natural and/or synthetic fibers. The body side liner can also be made of an oriented nonwoven as provided by this invention. The body side liner can be composed of a substantially hydrophobic material, and the hydrophobic material can, optionally, be treated with a surfactant or otherwise processed to impart a desired level of wettability and hydrophilicity. For example, the material can be surface treated with about 0.45 weight percent of a surfactant mixture comprising Ahcovel N-62 from Hodgson Textile Chemicals of Mount Holly, N.C. U.S.A. and Glucopan 220UP from Henkel Corporation of Ambler, Pa. in an active ratio of 3:1. The surfactant can be applied by any conventional means, such as spraying, printing, brush coating or the like. The surfactant can be applied to the entire body side liner 42 or can be selectively applied to particular sections of the body side liner, such as the medial section along the longitudinal centerline.

A suitable liquid permeable body side liner 42 is a nonwoven bicomponent web having a basis weight of about 27 gsm. The nonwoven bicomponent can be a spunbond bicomponent web, or a bonded carded bicomponent web. Suitable bicomponent staple fibers include a polyethyene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like.

The absorbent assembly 44 (FIG. 3) is positioned between the outer cover 40 and the body side liner 42, which components can be joined together by any suitable means such as adhesives, ultrasonic bonds, thermal bonds, or the like. The absorbent assembly 44 can be any structure which is generally compressible, conformable, non-irritating to the child's skin, and capable of absorbing and retaining liquids and certain body wastes. The absorbent assembly 44 can be manufactured in a wide variety of sizes and shapes, and from a wide variety of liquid absorbent materials commonly used in the art. For example, the absorbent assembly 44 can suitably comprise a matrix of hydrophilic fibers, such as a web of cellulose fluff, mixed with particles of a high-absorbency material commonly known as superabsorbent material. In a particular embodiment, the absorbent assembly 44 comprises a matrix of cellulosic fluff, such as wood pulp fluff, and superabsorbent hydrogel-forming particles. The wood pulp fluff can be exchanged with synthetic, polymeric, meltblown fibers or short cut homofilament or bicomponent synthetic fibers and natural fibers. The superabsorbent particles can be substantially homogeneously mixed with the hydrophilic fibers or can be nonuniformly mixed. The fluff and superabsorbent particles can also be selectively placed into desired zones of the absorbent assembly 44 to better contain and absorb body exudates. The concentration of the superabsorbent particles can also vary through the thickness of the absorbent assembly 44. Alternatively, the absorbent assembly 44 can comprise a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as cross-linked polymers, for example, sodium neutralized polyacrylic acid. Suitable superabsorbent materials are available from various commercial vendors, such as Dow Chemical Company located in Midland, Mich. U.S.A., and Stockhausen GmbH & Co. KG, D47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent assembly 44 is generally rectangular in shape, and comprises a blend of wood pulp fluff and superabsorbent material. One preferred type of pulp is identified with the trade designation CR1654, available from U.S. Alliance, Childersburg, Ala. U.S.A., and is a bleached, highly absorbent sulfate wood pulp containing primarily soft wood fibers and about 16 percent hardwood fibers. As a general rule, the superabsorbent material is present in the absorbent assembly 44 in an amount of from about 5 to about 90 weight percent based on total weight of the absorbent assembly. The absorbent assembly 44 suitably has a density within the range of about 0.10 to about 0.35 grams per cubic centimeter. The absorbent assembly 44 may or may not be wrapped or encompassed by a suitable tissue wrap that may help maintain the integrity and/or shape of the absorbent assembly.

The absorbent body 32 can also incorporate other materials that are designed primarily to receive, temporarily store, and/or transport liquid along the mutually facing surface with absorbent assembly 44, thereby maximizing the absorbent capacity of the absorbent assembly. One suitable material is referred to as a surge layer (not shown) and comprises a material having a basis weight of about 50 to about 120 grams per square meter, and comprising a through-air-bonded-carded web of a homogenous blend of 60 percent 3 denier type T-256 bicomponent fiber comprising a polyester core/polyethylene sheath and 40 percent 6 denier type T-295 polyester fiber, both commercially available from Kosa Corporation of Salisbury, N.C. U.S.A.

As noted previously, the illustrated training pant 20 has front and back side panels 34 and 134 disposed on each side of the absorbent body 32. These transversely opposed front side panels 34 and transversely opposed back side panels 134 can be permanently bonded along attachment lines 66 to the composite structure 33 of the absorbent body 32 in the respective front and back waist regions 22 and 24. More particularly, as shown best in FIGS. 2 and 3, the front side panels 34 can be permanently bonded to and extend transversely beyond the linear side edges 47 of the composite structure 33 in the front waist region 22, and the back side panels 134 can be permanently bonded to and extend transversely beyond the linear side edges of the composite structure in the back waist region 24. The side panels 34 and 134 may be attached using attachment means known to those skilled in the art such as adhesive, thermal or ultrasonic bonding. Alternatively, the side panels 34 and 134 can be formed as a portion of a component of the composite structure 33. For example, the side panels can comprise a generally wider portion of the outer cover, the body side liner, and/or another component of the absorbent body.

The side panels 34 and 134 preferably have elastic properties with sufficient extensibility to allow the wearer to pull the product up without having to open the fasteners on the pant. The side panels 34 and 134 also preferably provide sufficient retraction tension at extensions normally seen during wear to ensure good fit during wear without adjusting the fastener position. If the outer cover 40, as described above, comprises an elastic material, the side panels 34 and 134 may require less extensibility. Alternately, the pant may have an all-over stretch material across the entire width of the pant, comprising the outer cover 40 and side panels 34 and 134 as a single material component. The extension requirements of the side panels 34 and 134 are determined by the desired fit range for the product and the interaction with extension of other components, e.g., outer cover 40.

The illustrated side panels 34 and 134 each define a distal edge 68 that is spaced from the attachment line 66, a leg end edge 70 disposed toward the longitudinal center of the training pant 20, and a waist end edge 72 disposed toward a longitudinal end of the training pant. The leg end edge 70 and waist end edge 72 extend from the side edges 47 of the composite structure 33 to the distal edges 68. The leg end edges 70 of the side panels 34 and 134 form part of the side edges 36 of the absorbent body 32. In the back waist region 24, the leg end edges 70 are desirably although not necessarily curved and/or angled relative to the transverse axis 49 to provide greater coverage toward the back of the pant as compared to the front of the pant. The waist end edges 72 are desirably parallel to the transverse axis 49. The waist end edges 72 of the front side panels 34 form part of the front waist edge 38 of the absorbent body 32, and the waist end edges 72 of the back side panels 134 form part of the back waist edge 39 of the absorbent body.

In particular embodiments for improved fit and appearance, the side panels 34 and 134 desirably have an average length dimension measured parallel to the longitudinal axis 48 that is about 20 percent or greater, and particularly about 25 percent or greater, of the overall length dimension of the absorbent article, also measured parallel to the longitudinal axis 48. For example, in training pants having an overall length dimension of about 54 centimeters, the side panels 34 and 134 desirably have an average length dimension of about 10 centimeters or greater, such as about 15 centimeters. While each of the side panels 34 and 134 extend from the waist opening 50 to one of the leg openings 52, the back side panels 134 have a continually decreasing length dimension moving from the attachment line 66 to the distal edge 68, as is best shown in FIGS. 2 and 3.

Each of the side panels 34 and 134 can include one or more individual, distinct pieces of material. In particular embodiments, for example, each side panel 34 and 134 can include first and second side panel portions that are joined at a seam, or can include a single piece of material which is folded over upon itself (not shown). The side panels 34 and 134 desirably although not necessarily comprise an elastic material capable of stretching in a direction generally parallel to the transverse axis 49 of the training pant 20. Suitable elastic materials, as well as one process of incorporating elastic side panels into a training pant, are described in the following U.S. Pat. Nos. 4,940,464 issued Jul. 10, 1990 to Van Gompel et al.; 5,224,405 issued Jul. 6, 1993 to Pohjola; 5,104,116 issued Apr. 14, 1992 to Pohjola; and 5,046,272 issued Sep. 10, 1991 to Vogt et al.; all of which are incorporated herein by reference. In particular embodiments, the elastic material comprises a stretch-thermal laminate, a neck-bonded laminate, a reversibly necked laminate, or a stretch-bonded laminate material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; and European Patent Application No. EP 0 217 032 published on Apr. 8, 1987 in the names of Taylor et al.; all of which are incorporated herein by reference. Alternatively, the side panel material may comprise other woven or nonwoven materials, such as those described above as being suitable for the outer cover 40 or body side liner 42; mechanically prestrained materials; or extensible but inelastic materials.

In particular embodiments, one or more of the side panels 34 and 134 can be formed of retractive materials. For example, the side panels 34 and 134 can be formed of an elastomeric material that is adapted to retract upon activation by a source of heat, such as disclosed in U.S. Pat. No. 4,640,726.

The illustrated training pant 20 includes a fastening system 80 for refastenably securing the training pant about the waist of the wearer. The illustrated fastening system 80 includes first fastening components 82 and 83 that are adapted to refastenably connect to mating second fastening components 84 and 85. In one embodiment, one surface of each of the first fastening components 82 and 83 comprises a plurality of engaging elements that project from that surface. The engaging elements of the first fastening components 82 and 83 are adapted to repeatedly engage and disengage engaging elements of the second fastening components 84 and 85.

In one particular embodiment, the first fastening components 82 and 83 each comprise hook type fasteners and the second fastening components 84 and 85 each comprise complementary fasteners formed of oriented nonwoven loop material. In another particular embodiment, the first fastening components 82 and 83 each comprise fasteners formed of oriented nonwoven loop material and the second fastening components 84 and 85 each comprise complementary hook type fasteners. Although the illustrated embodiments show the back waist region 24 overlapping the front waist region 22, which is convenient, the training pant 20 can also be configured so that the front waist region overlaps the back waist region.

In alternative embodiments contemplated by this invention, fasteners 82-85 can be located anywhere over the front or back regions 22 and 24 of the pant. The fasteners 82-85 can be integral to any of the materials on the pant in the front or back regions 22 and 24. The fasteners can be integral to the entire outer cover of the pant (e.g. in a one piece outer cover product) or integral to the entire liner in the pant. The fasteners can be integral to panels 34 and/or 134.

Hook type fasteners typically comprise a fabric or material having a base or backing structure and a plurality of hook members extending upwardly from at least one surface of the backing structure. The hook material advantageously comprises a resilient material to minimize unintentional disengagement of the fastener components as a result of the hook material becoming deformed and catching on clothing or other items. The term "resilient" as used herein refers to an interlocking material having a predetermined shape and the property of the interlocking material to resume the predetermined shape after being engaged and disengaged from a mating, complementary interlocking material. Suitable hook material can be molded or extruded of nylon, polypropylene or another suitable material. Suitable single-sided hook materials for the fastening components 82-85 are available from commercial vendors such as Velcro Industries B.V., Amsterdam, Netherlands or affiliates thereof, and are identified as Velcro HTH-829 with a unidirectional hook pattern and having a thickness of about 0.9 millimeters (35 mils) and HTH-851 with a unidirectional hook pattern and having a thickness of about 0.5 millimeters (20 mils); and Minnesota Mining & Manufacturing Co., St. Paul, Minn. U.S.A., including specific materials identified as CS-600.

Figure 8:
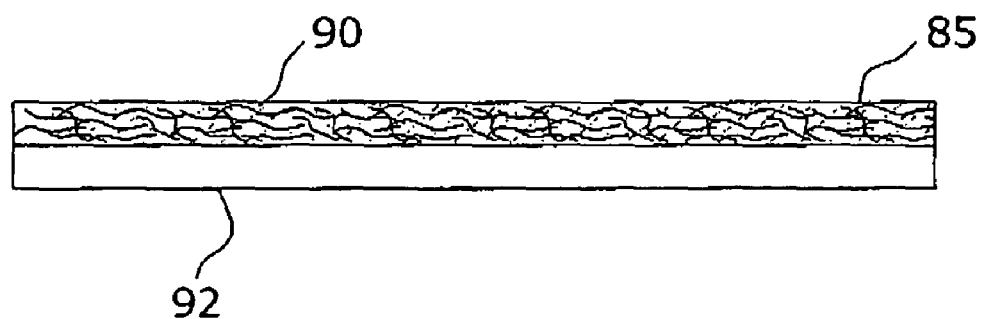
FIG. 8 is a schematic side elevation of a loop fastener of the present invention comprising an oriented nonwoven loop material secured to a substrate.

In accordance with the present invention, the loop type fastener (e.g., fastener 84, 85) is preferably made of an oriented material, and more preferably an oriented material comprising a nonwoven web of substantially continuous fibers. As illustrated in FIG. 8, the oriented material can comprise an oriented, extensible material, and particularly, an oriented, extensible material 90 attached to an elastic substrate 92 so that the composite is extensible and provides retraction tension over a suitable range of extensions. With particular reference to FIG. 3, the first fastening components 82 and 83 are desirably although not necessarily disposed on the inner surface 28 of the training pant 20 in the back waist region 24. The first fastening components 82 and 83 are desirably positioned along the distal edges 68 of the back side panels 134, and abutting or adjacent to the waist end edge 72. In certain embodiments, for example, the first fastening components 82 and 83 can be located within about 2 centimeters, and more particularly within about 1 centimeter, of the distal edges 68, the waist end edges 72, and the leg end edges 70.

With particular reference to FIG. 2, the second fastening components 84 and 85 are desirably although not necessarily disposed on the outer surface 30 of the training pant 20 in the front waist region 22. The second fastening components 84 and 85 are sized to receive the first fastening components 82 and 83 and are desirably positioned along the distal edges 68 of the front side panels 34, and abutting or adjacent to the waist end edge 72. In certain embodiments, for example, the second fastening components 84 and 85 can be located within about 2 centimeters, and more particularly within about 1 centimeter, of the distal edges 68, the waist end edges 72, and the leg end edges 70. Where the first fastening components 82 and 83 comprise loop type fasteners disposed on the inner surface 28 and the second fastening components 84 and 85 comprise hook type fasteners disposed on the outer surface 30, the first fastening components can be sized larger than the second fastening components to ensure coverage of the rigid, outwardly-directed hooks. The loop fastening components can be integral with the side panels or adhered to the side panels 34 and 134 by any means known to those skilled in the art such as adhesive bonds, sonic bonds or thermal bonds. The loop fastening components can be extensible and bonded in overlaying relationship onto any layer of the body 32 in a manner that retains the extension and retraction characteristics of the loop fastening components.

The fastening components are desirably rectangular, although they may alternatively be square, round, oval, curved or otherwise non-rectangular in shape. In particular embodiments, each of the fastening components 82-85 defines a length dimension aligned generally parallel with the longitudinal axis 48 of the training pant 20 and a width dimension aligned generally parallel with the transverse axis 49 of the training pant. For a child of about 9 to about 15 kilograms (20-33 pounds), for example, the length dimension of the fastening components is desirably from about 5 to about 13 centimeters, such as about 10 centimeters, and the width dimension is desirably from about 0.5 to about 3 centimeters, such as about 1 centimeter. With particular embodiments, the fastening components can have a length-to-width ratio of about 2 or greater, such as about 2 to about 25, and particularly about 5 or greater, such as about 5 to about 8. For other embodiments such as for adult products, it may be desirable for one or more of the fastening components to comprise a plurality of relatively smaller fastening elements. In that case, a fastening component or individual fastening elements may have an even smaller length-to-width ratio, for example, of about 2 or less, and even about 1 or less.

When the fastening components 82-85 are releasably engaged, the side edges 36 of the absorbent body 32 in the crotch region 26 define the leg openings 52, the waist edges 38 and 39 of the absorbent body, including the waist end edges 72 of the side panels, define the waist opening 50, and the waist regions 22 and 24 jointly define a waistband 75 and hip section 77. For improved formation of the leg openings 52, it can be desirable in some embodiments for the front side panels 34 to be longitudinally spaced from the back side panels 134 (see FIGS. 2 and 3). For example, the front side panels 34 can be longitudinally spaced from the back side panels 134 by a distance equal to about 20 percent or greater, particularly from about 20 to about 60 percent, and more particularly from about 35 to about 50 percent, of the overall length dimension of the absorbent article.

When connected, the fastening components 82-85 form refastenable seams 88 (FIG. 1) that desirably although not necessarily extend substantially the entire distance between the waist opening 50 and the leg openings 52. More specifically, the refastenable seams 88 can cover about 80 to 100 percent, and particularly about 90 to about 98 percent, of the distance between the waist opening 50 and each leg opening 52, which distance is measured parallel to the longitudinal axis 48. To construct the seams 88 to extend substantially the entire distance between the waist and leg openings 50 and 52, the fastening components 82-85 can be formed to cover about 80 to 100 percent, and more particularly about 90 to about 98 percent, of the distance between the waist end edge 70 and the leg end edge 72 of the side panels 34 and 134. In other embodiments, the fastening components can comprise a plurality of smaller fastening elements covering a smaller portion of the distance between the waist opening 50 and the leg openings 52, for example, about 20 to about 70 percent, but spaced apart to span a larger percentage of the distance between the waist opening and the leg openings.

It is also contemplated that the fastening components 82-85 may be incorporated as integral portions of the pant rather than separate components applied during manufacture. If the fastening components 82 and 83, are a single component and are integral to the pant in the front region 22, for example, the size and the shape of the fastening component is directly equal to the size and shape of that region. If the fastening components 82-85 are integral parts of side panels 34 and/or 134, for another example, the fastening components are the same size and shape as the side panels 34 and/or 134.

For the refastenable seams 88 to be located at the sides of the wearer, it can be particularly desirable for the transverse distance between the first fastening components 82 and 83 to be substantially equal to the transverse distance between the second fastening components 84 and 85. The transverse distance between a set of fasteners is the distance measured parallel to the transverse axis 49 between the longitudinal centerlines of the fasteners, measured with the side panels 34 and 134 in their relaxed, or non-extended, condition. In an alternative embodiment, the training pant 20 includes only a single second fastening component disposed in the front waist region 22 for refastenably connecting the first fastening components 82 and 83 (not shown).

Figure 4:
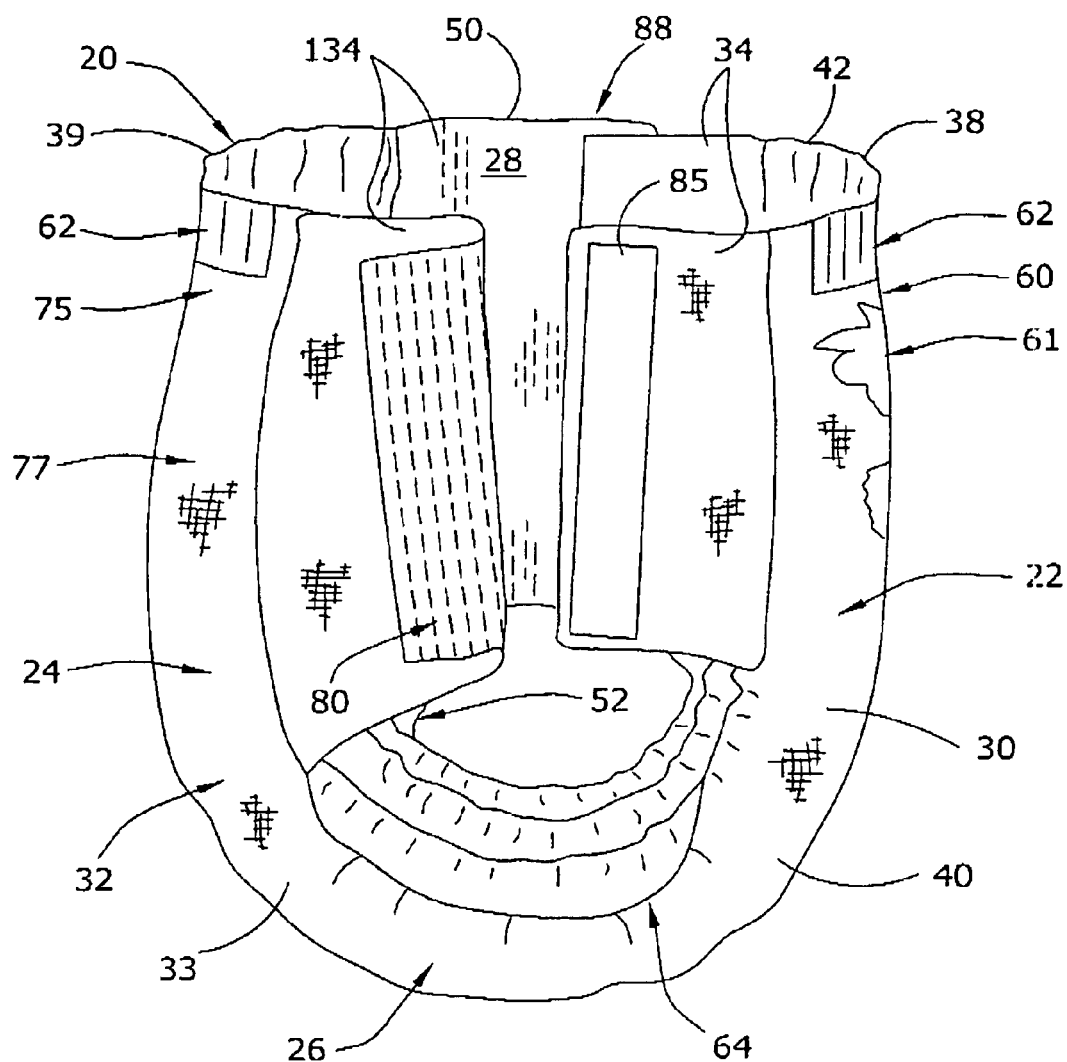
FIG. 4 illustrates an alternative embodiment of the present invention in a side view similar to FIG. 1.
Figure 5:
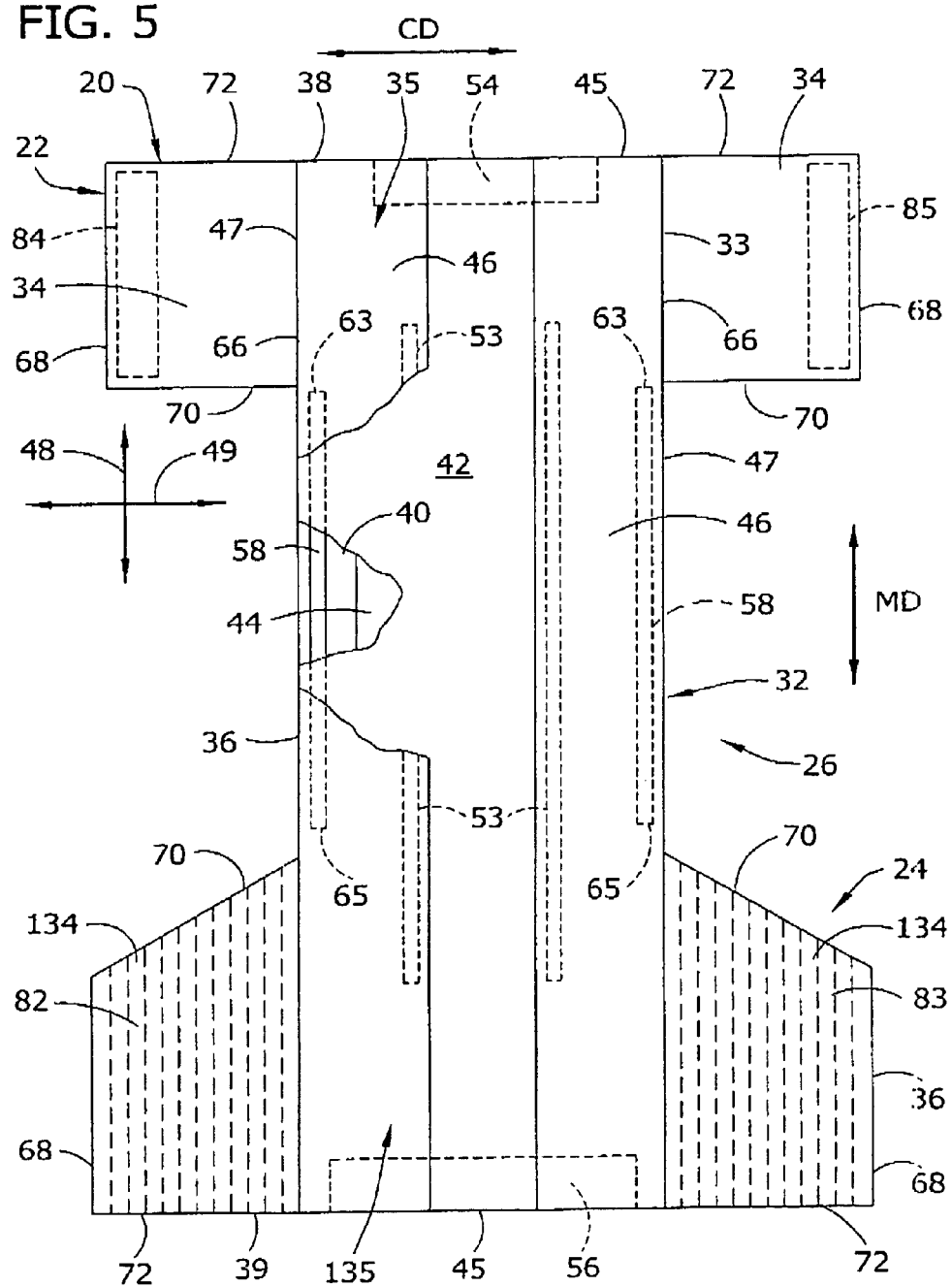
FIG. 5 is a plan view of the embodiment of FIG. 4 in a similar position as FIG. 3.

In a further alternative embodiment illustrated in FIGS. 4 and 5, one or both of the fastening components can comprise integral portions of the waist regions. For instance, the front and back side panels 34 and 134 can function as fastening components in that they can comprise a material that is releasably engageable with complementary fastening components disposed in the opposite waist region. As illustrated in FIGS. 4 and 5, the side panels 134 are made completely of extensible oriented loop material. Alternatively, these side panels could be made of oriented loop material only at their outer edges where they will engage the hook material, and the remainder of the side panels can be made of some other, preferably extensible, material and joined along abutting edges thereof.

Figure 6:
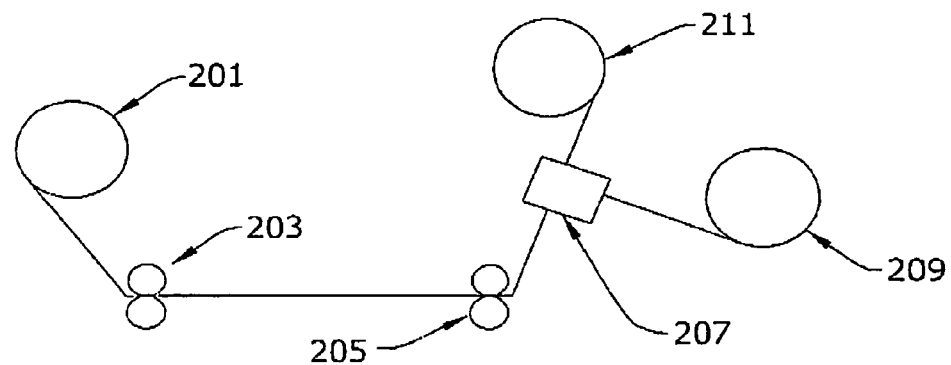
FIG. 6 schematically illustrates a flow diagram for manufacture of one embodiment of the oriented nonwoven loop material used in a pant according to the present invention. This process would make a material oriented in the machine direction.

FIG. 6 schematically shows how a nonwoven can be drawn between two nips to orient the material. This drawing process also orients the fibers in the machine direction. Specifically, the drawing process of FIG. 6 orients the nonwoven in the machine direction. This drawing process also orients the nonwoven fibers to be more aligned in the machine direction than in the cross direction. A nonwoven material, illustrated in FIG. 6 as roll 201, of a certain width is fed into a nip point or a draw control section, as illustrated in FIG. 6 as nip 203. The draw control point 203 is running at a speed of x and controls the speed of the feeding nonwoven web. The nonwoven material is than drawn to a nip point or draw control point 205. Draw control point 205 is running faster than draw control point 203, which orients the nonwoven. The ratio of the speed of nip 205 to the speed of nip 203 is the draw ratio between the two nips. If the distance between nips 203 and 205 is relatively small, the drawing process does not substantially narrow, or neck, the web. If the distance between nips 203 and 205 is relatively large, the drawing process can narrow, or neck, the material in the cross direction to a greater extent. By adding nip points subsequent to nip 205, the material can be oriented and/or necked further. By controlling the distance between nips 203 and 205 and subsequent nips and the draw ratios between the nip points, the degree of orientation of the web in the machine direction and the degree of necking of the web in the cross direction can be controlled. The nonwoven material thus oriented (e.g., with more fibers oriented generally in the machine direction (i.e., the direction of the draw) can be wound on a base roll or attached by bonder 207 to another material 209. The bonding can be accomplished by hot melt adhesive, ultrasonic bonds, thermal bonds, or any means well known in the art of bonding. Attachment to a substrate may also be accomplished by direct extrusion of a substrate polymer onto the extended nonwoven, or by means of calendaring an extruded substrate directly to the extended nonwoven in a heated and/or patterned nip. The nonwoven can be wound to form a base roll 211 to later be unwound into another assembly process (such as making a disposable training pant). Alternatively, this process for producing the oriented nonwoven loop material can be an integral step in the assembling process for making a disposable training pant.

Figure 7:
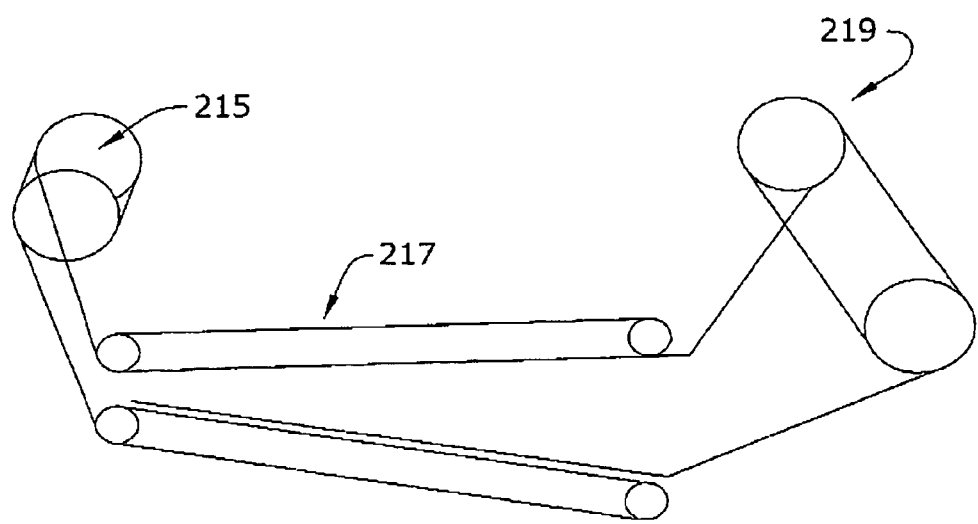
FIG. 7 schematically illustrates a flow diagram for manufacture of another embodiment of the oriented nonwoven loop material used in a pant according to the present invention. This would make a material oriented in the cross machine direction.

FIG. 7 schematically shows how a nonwoven can be drawn in the cross machine direction to orient the material and its constituent fibers in the cross machine direction. Thus, the cross machine direction drawing process illustrated in FIG. 7 orients the nonwoven in the cross machine direction and orients the fibers of the nonwoven in the cross machine direction. A nonwoven 215 is unwound or fed into a side stretching section 217. This side stretching section grips the side edges of the nonwoven and draws or extends the material in the cross machine direction as it moves in the machine direction of the drawing process. Side stretching section 217 may consist of multiple, sequential side stretching subsections. The nonwoven material can then be wound on a roll 219, or fed into another process such as a disposable pant assembly process, or laminated to another material to stabilize the orientation of the fibers in the cross machine direction.

Figure 9A:
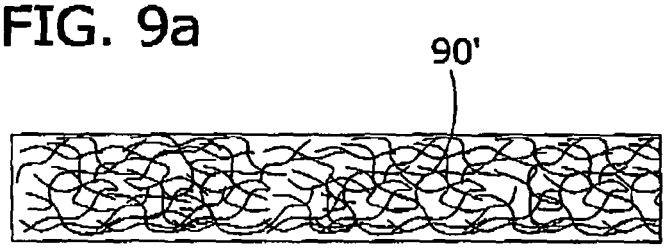
FIG. 9a is a top plan view of an orientable nonwoven loop material of the present invention prior to being oriented.
Figure 9B:
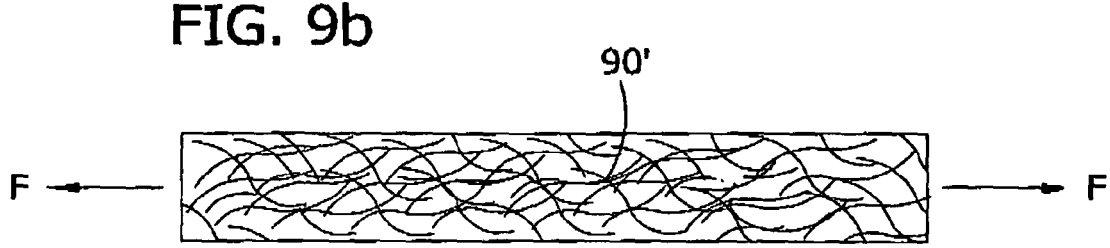
FIG. 9b is a top plan view of the nonwoven loop material of FIG. 9a being oriented by applying a force to the nonwoven loop material.
Figure 9C:
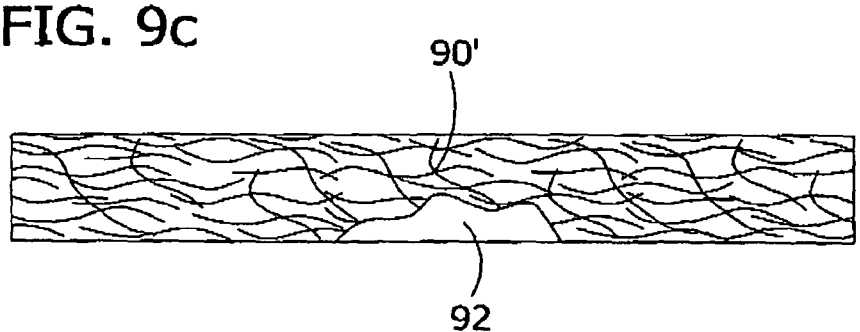
FIG. 9c is a top plan view of the nonwoven loop material showing that more of the constituent fibers of the oriented loop material are aligned in the direction of the force after the force was applied than were aligned in the direction of the force before the force was applied, the loop material being partially cut away to show the backing substrate to which the nonwoven loop material is secured.

FIG. 9a illustrates a non-oriented, non-woven loop material 90'. In other words, the nonwoven loop material 90' is shown before being oriented. As shown in FIG. 9b, the fibers of the nonwoven loop material 90' are oriented by extending the nonwoven loop material by applying a force F to the loop material. FIG. 9c illustrates the non-woven material following drawing (e.g., extension) thereof to orient fibers of the material in the direction of draw and securement of the material (e.g., material 90) to the substrate 92. By comparing the nonwoven loop material 90' before application of the force F as shown in FIG. 9a and the nonwoven loop material 90' after application of the force F as shown in FIG. 9c, it can be seen that more constituent fibers of the nonwoven loop material are aligned in the direction of force in FIG. 9c than in FIG. 9a.

The orientable material used to form the oriented nonwoven loop material can be made in accordance with the teachings of U.S. Pat. No. 4,965,122 incorporated herein by reference thereto. The orientable material may be formed by known nonwoven processes, such as, for example, meltblowing processes or spunbonding processes. If the orientable material is a web of meltblown fibers, it may include meltblown microfibers. The orientable material can be any material with a network of substantially continuous fibers or filaments that can be oriented upon application of a force in one direction without material failure, i.e., breaking or tearing.

The orientable material could be a multilayer material having, for example, at least one layer of spunbonded web joined to at least one layer of meltblown web, bonded carded web or other suitable material. For example, the orientable material may be a multilayer material having a first layer of spunbonded polypropylene having a basis weight from about 0.2 to about 8 ounces per square yard (osy), a layer of meltblown polypropylene having a basis weight from about 0.2 to about 4 osy, and a second layer of spunbonded polypropylene having a basis weight of about 0.2 to about 8 osy. Alternatively, the orientable material may be a single layer of material such as, for example, a spunbonded web having a basis weight of from about 0.2 to about 10 osy or a meltblown web having a basis weight of from about 0.2 to about 8 osy.

The orientable material may also be a composite material made of a mixture of two or more different fibers or a mixture of fibers and particulates. Such mixtures may be formed by adding fibers and/or particulates to a gas stream in which meltblown fibers are carried so that an intimate entangled commingling of substantially continuous meltblown fibers and other materials, e.g., wood pulp, staplefibers or particulates such as, for example, super-absorbent materials, occurs prior to collection of the fibers upon a collecting device to form a coherent web of randomly dispersed meltblown fibers and other materials, such as are disclosed in U.S. Pat. No. 4,100,324, the disclosure of which is hereby incorporated by reference.

If the orientable material is a nonwoven web of fibers, the fibers should be joined by interfiber bonding to form a coherent web structure which is able to withstand orienting. Interfiber bonding may be produced by entanglement between individual fibers. The fiber entangling is inherent in the meltblown process but may be generated or increased by processes such as, for example, hydraulic entangling or needle punching. Alternatively and/or additionally a bonding agent may be used to increase the desired bonding.

The oriented material may be stabilized if desired by one of a number of methods. Application of heat can be used to produce a "set" in a necked, oriented material, which provides a loop material that readily extends but has little retractive force upon extension. Alternatively, the oriented material may be attached to an extendable substrate, such as a film, with provides a loop material requiring somewhat greater force to extend, but will not retract after extension. If a non-extensible loop material is desired, the oriented material may be attached to a non-extensible substrate. If an elastic loop material having both extension and recovery characteristics normally associated with elastomeric materials is desired, an oriented, necked material should be attached to an elastic substrate.

The oriented material can be made into a neck-bonded laminate as taught in U.S. Pat. No. 4,981,747. The oriented material may be treated if it has been necked in the drawing process to instill a memory into the material to cause the material to retract from its extension as taught in U.S. Pat. No. 4,965,122. A method of treatment is the application of heat. Certain polymers such as, for example, polyolefins, polyesters and polyamides may be heat treated under suitable conditions to impart such memory. Exemplary polyolefins include one or more of polyethylene, polypropylene, polybutene, ethylene copolymers, propylene copolymers and butene copolymers. Polypropylenes that have been found useful include, for example, polypropylene available from the Himont Corporation under the trade designation PC-973, polypropylene available from the Exxon Chemical Company under the trade designation Exxon 3445, and polypropylene available from the Shell Chemical Company under the trade designation DX 5A09. Chemical characteristics of these materials are available from their respective manufacturers.

The relation between the original width of the orientable material to its width after tensioning determines the extension limits of the oriented material. For example, if it is desired to prepare a necked material that can be readily extended to a 150 percent elongation (i.e., 250 percent of its necked width) an orientable material having a width "A" such as, for example, 250 cm, is tensioned so that it necks down to a width "B" of about 100 cm for a percent neck or percent neckdown of about 60 percent. The resulting necked material has a width "B" of about 100 cm and is readily extensible to at least the original 250 cm dimension "A" of the orientable material for an elongation or percent stretch of about 150 percent. The necked material can be made into neck-bonded laminate material by laminating the necked material to an elastomer as taught in U.S. Pat. No. 5,336,545.

It is also contemplated that when the training pants or the like garment are being initially constructed and folded by machine, the loop material and/or its underlying support material of the various embodiments can be positioned over the hook material and then pressed thereon to give an initial construction that is stronger in the mechanical fastener system than conventional mechanical fastening systems.

While the mechanical fastening means of the present invention are shown and described herein in connection with children's toilet training pants, it is understood that such fastening means may be incorporated into various other disposable absorbent articles, such as diapers, adult incontinence garments, sanitary napkins and the like, as well as surgical bandages and sponges, without departing from the scope of the present invention.

As various changes could be made in the above constructions and methods, without departing from the scope of the invention, it is intended that all matter contained in the above description and shown in the accompanying drawings shall be interpreted as illustrative and not in a limiting sense.

When introducing elements of the present invention or the preferred embodiment(s) thereof, the articles "a", "an", "the"

and "said" are intended to mean that there are one or more of the elements. The terms "comprising", "including" and "having" are intended to be inclusive and mean that there may be additional elements other than the listed elements.

What is claimed is:

1. A mechanical fastening system for an article, said fastening system comprising:
   a first fastening component comprising an oriented nonwoven loop material secured to a substrate, the oriented nonwoven loop material comprising a nonwoven web of fibers in which a greater number of fibers are oriented in a selected direction by the application of a force in the selected direction to extend the web; and
   a second fastening component comprising a hook material, the oriented nonwoven loop material of the first fastening component being adapted for releaseable connection with the hook material of the second fastening component.

2. The mechanical fastening system of claim 1 wherein the nonwoven web has a machine direction and a cross-machine direction, the direction of extension of the nonwoven web being the machine direction of said nonwoven web.

3. The mechanical fastening system set forth in claim 1 wherein the nonwoven web comprises substantially continuous fibers. component being adapted for releasable connection with the hook material of the second fastening component.

4. The mechanical fastening system set forth in claim 1 in combination with the article, said substrate being formed integrally with the article.

5. The mechanical fastening system set forth in claim 1 wherein the substrate is substantially inelastic.

6. An absorbent article for personal wear, the absorbent article comprising:
   a liquid permeable inner layer for contact with a wearer's skin, an outer layer in superposed relationship with the inner layer, and an absorbent layer disposed between the inner layer and the outer layer, the article having a first end region and a second end region; and
   a mechanical fastening system comprising at least one first fastening component disposed generally at the first end region of the article and at least one second fastening component disposed generally at the second end region of said article and adapted for releasable connection with the at least one first fastening component to secure the article on the wearer of said article, the at least one first fastening component comprising an oriented nonwoven loop material secured to a substrate, the oriented nonwoven loop material comprising a nonwoven web of fibers in which a greater number of fibers are oriented in a selected direction by the application of a force in the selected direction to extend the web, the at least one second fastening component comprising a hook material, the oriented nonwoven loop material of the at least one first fastening component being adapted for releasable connection with the hook material of the at least one second fastening component.

7. The absorbent article set forth in claim 6 wherein the nonwoven web is generally free from substantial necking and gathering in a direction perpendicular to the direction in which the web is extended.

8. The absorbent article set forth in claim 6 wherein the substrate is formed integrally with the article.

9. The absorbent article set forth in claim 6 wherein the substrate is substantially inelastic.

10. The absorbent article set forth in claim 6 wherein the nonwoven web of the at least one first fastening component has a machine direction and a cross-machine direction, the direction in which the web is extended being the machine direction.

11. A mechanical fastening system for an article, said fastening system comprising:
    a first fastening component comprising a loop material formed by a nonwoven web of fibers, the fibers in the nonwoven web being oriented by drawing of the nonwoven web of fibers in a direction so that more of the fibers are oriented in the direction of drawing than prior to drawing of the nonwoven web of fibers; and
    a second fastening component comprising a hook material, the oriented nonwoven loop material of the first fastening component being adapted for releasable connection with the hook material of the second fastening component.

12. The mechanical fastening system set forth in claim 11 in combination with the article, the first fastening component defining at least a portion of said article.

13. A mechanical fastening system for an article, said fastening system comprising:
    a first fastening component comprising a loop material formed by a nonwoven web of fibers, the fibers in the nonwoven web being oriented by application of force to the nonwoven web of fibers in a direction so that more of the fibers are oriented in the direction of force than prior to applying a force to the nonwoven web of fibers; and
    a second fastening component comprising a hook material, the oriented nonwoven loop material of the first fastening component being adapted for releasable connection with the hook material of the second fastening component.

14. The mechanical fastening system set forth in claim 13 in combination with the article, the first fastening component defining at least a portion of said article.

* * * * *